(12) United States Patent
Gauthier et al.

(10) Patent No.: US 11,299,896 B2
(45) Date of Patent: Apr. 12, 2022

(54) SELF-CONTAINED TREATMENT UNIT FOR HAEMODIALYSIS TREATMENTS

(71) Applicant: HEMO PLUS SÀRL, Lausanne (CH)

(72) Inventors: Henri Gauthier, Toulouse (FR); Nicolas Tilatti, Boe (FR); Philippe Courtiade, Aigrefeuille (FR)

(73) Assignee: HEMO PLUS SÀRL, Lausanne (CH)

( * ) Notice: Subject to any disclaimer, the term of this patent is extended or adjusted under 35 U.S.C. 154(b) by 0 days.

(21) Appl. No.: 16/930,770

(22) Filed: Jul. 16, 2020

(65) Prior Publication Data

US 2020/0347627 A1  Nov. 5, 2020

Related U.S. Application Data

(63) Continuation of application No. 16/300,110, filed as application No. PCT/CH2017/000070 on Jul. 4, 2017, now abandoned.

(30) Foreign Application Priority Data

Jul. 5, 2016 (CH) ..................................... 00852/16

(51) Int. Cl.
*E04H 3/08* (2006.01)
*E04H 1/00* (2006.01)
(Continued)

(52) U.S. Cl.
CPC ............. *E04H 3/08* (2013.01); *A61M 1/1666* (2014.02); *E04B 1/34807* (2013.01);
(Continued)

(58) Field of Classification Search
CPC ......... E04H 3/08; E04H 1/1205; E04H 1/125; E04H 1/005; A61M 1/1666; A61M 1/16;
(Continued)

(56) References Cited

U.S. PATENT DOCUMENTS 4,599,829 A  7/1986 DiMartino, Sr.
4,779,514 A  10/1988 Prigmore et al.
(Continued)

FOREIGN PATENT DOCUMENTS

DE  20 2013 1 02 296 U1  8/2013
WO     03/095765 A1  11/2003
(Continued)

*Primary Examiner* — Brent W Herring
(74) *Attorney, Agent, or Firm* — Finch & Maloney, PLLC; Michael Bujold; Jay Franklin

(57) ABSTRACT

An autonomous treatment unit (10, 200) for treating at least a plurality of patients by hemodialysis. The unit being an individual construction comprising at least one care room equipped with a dialysis generator to prepare treatment solutions of at least one of sodium chloride, potassium chloride, calcium chloride, and magnesium chloride with hemodialysis water for each individual patient. The treatment unit is a housing structure grouping of a plurality of elementary modules built substantially in a same way, juxtaposed and arranged internally, individually or in a combination, to form a first group of service rooms (210) assigned for hemodialysis treatment of patients, reception of patients, administrative follow-up of patients and medical follow-up of patients. A second group of rooms (250) for preparation and storage of the concentrates, the fluids used in the care rooms and/or the reprocessing and/or disposal of the residual and effluents generated treatments generated by the treatment.

4 Claims, 5 Drawing Sheets

(51) Int. Cl.
*E04H 1/12* (2006.01)
*E04B 1/348* (2006.01)
*A61M 1/16* (2006.01)

(52) U.S. Cl.
CPC ............. *E04H 1/005* (2013.01); *E04H 1/125* (2013.01); *E04H 1/1205* (2013.01)

(58) Field of Classification Search
CPC ............. A61M 1/1656; E04B 1/34807; E04B 9/0421; F24F 5/0003
USPC .................................................. 52/234, 79.1
See application file for complete search history.

(56) References Cited

U.S. PATENT DOCUMENTS

| | | |
|---|---|---|
| 5,727,353 A | 3/1998 | Getz et al. |
| 5,775,758 A * | 7/1998 | Eberspacher ............ B60P 3/14 296/19 |
| 5,964,065 A | 10/1999 | Migurski et al. |
| 6,179,358 B1 | 1/2001 | Hirayama et al. |
| 6,243,993 B1 | 6/2001 | Swensson |
| 6,256,936 B1 | 7/2001 | Swensson et al. |
| 7,794,001 B2 | 9/2010 | Blackwell et al. |
| 8,042,562 B1 | 10/2011 | McDaniel, Jr. |
| 9,127,470 B2 | 9/2015 | Lee |
| 10,161,147 B2 | 12/2018 | Jornitz |
| 10,428,540 B1 | 10/2019 | Werner et al. |
| 10,533,758 B2 | 1/2020 | Jornitz et al. |
| 2010/0024352 A1 | 2/2010 | Pope |
| 2011/0053486 A1 | 3/2011 | Holtz et al. |
| 2011/0120035 A1 | 5/2011 | Staebler |
| 2011/0173898 A1 | 7/2011 | Denicourt et al. |
| 2013/0154296 A1 | 6/2013 | Blackwell et al. |
| 2014/0290151 A1 | 10/2014 | Lee |
| 2016/0010883 A1 | 1/2016 | Jornitz et al. |
| 2016/0128886 A1 | 5/2016 | Merino et al. |
| 2017/0130447 A1 | 5/2017 | Lane, Jr. et al. |
| 2017/0333267 A1 | 11/2017 | Anandasabapathy et al. |

FOREIGN PATENT DOCUMENTS

| | | |
|---|---|---|
| WO | 2004/003934 A1 | 1/2004 |
| WO | 2010/001418 A1 | 1/2010 |

* cited by examiner

SELF-CONTAINED TREATMENT UNIT FOR HAEMODIALYSIS TREATMENTS

This application is a continuation of U.S. patent application Ser. No. 16/300,110 filed Nov. 9, 2018, which is a National Stage completion of PCT/CH2017/000070 filed Jul. 4, 2017, which claims priority from Swiss patent application serial no. 00852/16 filed Jul. 5, 2016.

FIELD OF THE INVENTION

This invention relates to a treatment center for treating by hemodialysis, simultaneously or successively, a plurality of patients, said center comprising at least one care unit equipped with a dialysis generator, said dialysis generator being arranged to prepare a treatment solution adapted to each of said patients of said plurality of patients, said treatment solution being prepared by dilution with hemodialysis water of at least one concentrate made of solid water-soluble compounds, said solid compounds comprising at least sodium chloride (NaCl), potassium chloride (KCl), calcium chloride ($CaCl_2$), and magnesium chloride ($MgCl_2$).

BACKGROUND OF THE INVENTION

The hemodialysis patient treatment centers are often integrated in a hospital or clinic, in the form of a department assigned to this treatment. It appears that these departments are structured differently according to the hospitals and that the administrative organization and the medical follow-up of the patients must be designed on a case-by-case basis. Moreover, depending on the concerned medical centers, the available space is variable, so that the ancillary services such as the storage of the basic products, the treatment of the water intended for preparing the hemodialysis solutions from concentrates, the treatment and disposal of the waste, are scattered because of their diversification, which makes both treatment follow-up and patient safety complicated.

Now, the treatment of patients by hemodialysis is a long-term repetitive process, as a dialysis patient is usually treated at least twice a week and the interventions take place for months or even years, often life long, almost the same way. This implies that every treatment requires substantially the same operations, the same preparations, the same control before, during and after the treatment, so that a streamlining of the processes and a standardization of the equipment show to be helpful both to simplify the operations, to better control and monitor them, to better ensure patient safety and to better constitute and/or complete the medical record of each of the patients so as to have at any time an updated record of every patient.

In large medical centers, many affections are treated and the ancillary services must be widely diversified to meet the demand of the various departments corresponding to the various assignments. In smaller departments, which can sometimes be located far from a large center, one recognizes the interest to have on site the whole of the infrastructures required to ensure the treatments. This is in particular the case for the hemodialysis treatments, which are carried out in large centers supplied by central concentrates production units, unlike small centers where, for profitability and efficiency reasons, a local concentrates production is recommended or even imposed.

This invention allows reaching these goals by realizing a care center for hemodialysis patient treatment which is a model perfectly adapted to this treatment, which can be reproduced at any location while keeping flexibility in terms of the size of the patients treatment area itself, according to the geographic location of the installation site, of the demographics and of the locally available means.

The care center according to the invention ideally belongs to a group of substantially identical care centers, which are installed on a territory located more or less around a production unit of concentrates for hemodialysis patient treatment. This concept allows simplifying and rationalizing significantly the supply of the treatment centers, makes the treatment less expensive and less risky, while ensuring a regular supply on demand of the care units and a distribution that allows reducing the risks linked with the transport. It also allows bringing the care centers closer to the patients insofar as they do not need pre-existing hospital or clinic facilities. Their autonomy allows locating them outside or inside pre-existing buildings, but which have no specific medical status.

Nevertheless, in the case of smaller units, or if they are very far away from the concentrates production center, an integrated service can be arranged in the care center to produce the required concentrates on site.

SUMMARY OF THE INVENTION

This is why this invention offers to realize a treatment center able to provide a solution to all of the problems mentioned above.

This goal is achieved by the treatment center according to the invention as defined in the preamble and characterized in that said treatment center is built in a hosting structure grouping a plurality of elementary modules built substantially the same way, juxtaposed and arranged internally, individually or in a combination, to form at least one care room for a hemodialysis treatment of said plurality of patients, and dedicated rooms arranged respectively to ensure the reception of the patients, the administrative follow-up of the patients, the medical follow-up of the patients, the storage of the concentrates, the preparation and control of the fluids used in said care room and/or the reprocessing and/or disposal of the residual waste and effluents generated by the treatment of the patients.

According to a preferred embodiment, the care unit includes a care room for hemodialysis treatment that is mounted in at least one elementary module and contains at least one seat or bed for treating a patient, associated with a set of technical treatment components including a hemodialysis generator, a device for the connection to an electrical power supply network, a device for the connection to a data processing network, a device for the connection to a hemodialysis water supply, a device for the connection to a hemodialysis concentrates supply and a waste collection device.

Said hemodialysis generator is preferably arranged to produce a solution adapted to a specific patient by taking a predetermined quantity of at least one hemodialysis concentrate and a predetermined volume of hemodialysis water, and mix these components in order to prepare and inject said solution adapted to said specific patient throughout the treatment.

In a particularly advantageous way, said care room for a hemodialysis treatment includes two places and contains two treatment seats or beds arranged facing each other for the simultaneous treatment of two patients, each of said seats or beds being associated to a set of technical treatment components.

In order to ensure both the transport and mounting of the care unit, each elementary module can comprise a rigid frame on which closing and/or separating walls are mounted, in which said rigid frame comprises, in its upper section, an empty space to contain technical components.

Said empty space contains preferably at least one purified air supply duct and at least one ambient air exhaust duct, as well as a circulation circuit for heated or refrigerated liquid to ensure air conditioning inside of said treatment room.

According to a preferred embodiment, said care room is arranged substantially in the center of said hosting structure, which comprises on the one hand a first set of elementary modules making up first dedicated rooms, assembled to be arranged as a patient reception room, an administrative formalities room, a medical care room, and a second set of elementary modules making up second dedicated rooms, assembled to be arranged as a concentrate solutions storage room, a water treatment room, a pharmaceutical products storage room, an electrical energy management room and a waste processing/disposal room.

Said care room for a hemodialysis treatment comprises at least one elementary module assigned to the treatment of patients with particular contaminations, which require medical precautions to protect the other patients and/or the caregivers, said elementary module having a secured access.

Said rigid frame on which closing and/or separating walls are mounted is a metal frame and said closing and/or separating walls are made out of thermally insulated composite material panels covered with impervious finishing materials.

The rigid frames of the juxtaposed elementary modules are preferably assembled in such a way that each dedicated room has a surface adapted to its function and the closing/separating walls are mounted on said rigid frames in order to geometrically delimit said surface adapted to the function assigned to said room.

Each of the elementary modules comprises a double ceiling that defines said free space on top of the care rooms and of the dedicated rooms, said free space being used for channels and/or technical ducts.

Said technical room advantageously comprises at least means for receiving and storing raw materials, a removal unit, weighing means, a preparation unit for the patient's treatment solutions, a filtration unit and a unit for filling the containers intended for concentrates storage.

BRIEF DESCRIPTION OF THE DRAWINGS

The present invention and its advantages will be better revealed in the following description of an embodiment given as a non limiting example, in reference to the drawings in appendix, in which.

DETAILED DESCRIPTION OF THE PREFERRED EMBODIMENTS

Figure 1:
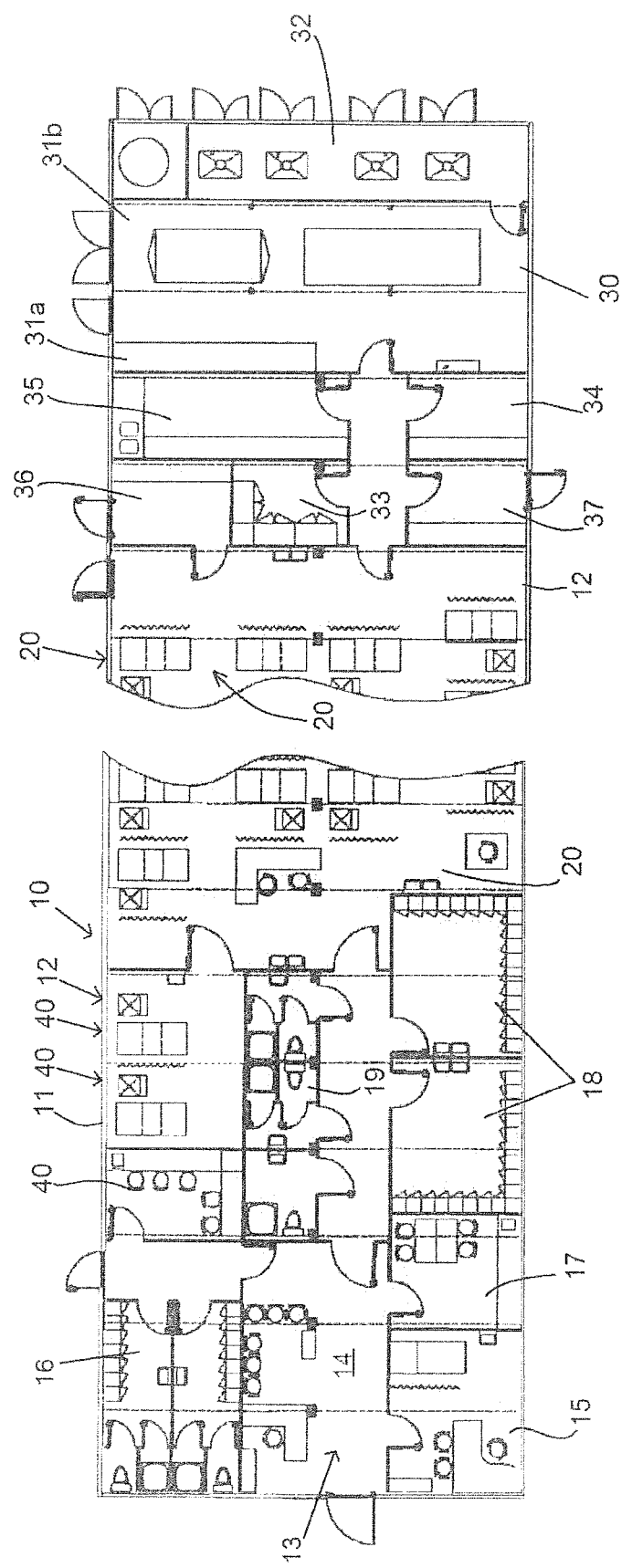
FIG. 1 is a schematic general view representing an embodiment of a hemodialysis care unit according to the invention.
Figure 2A:
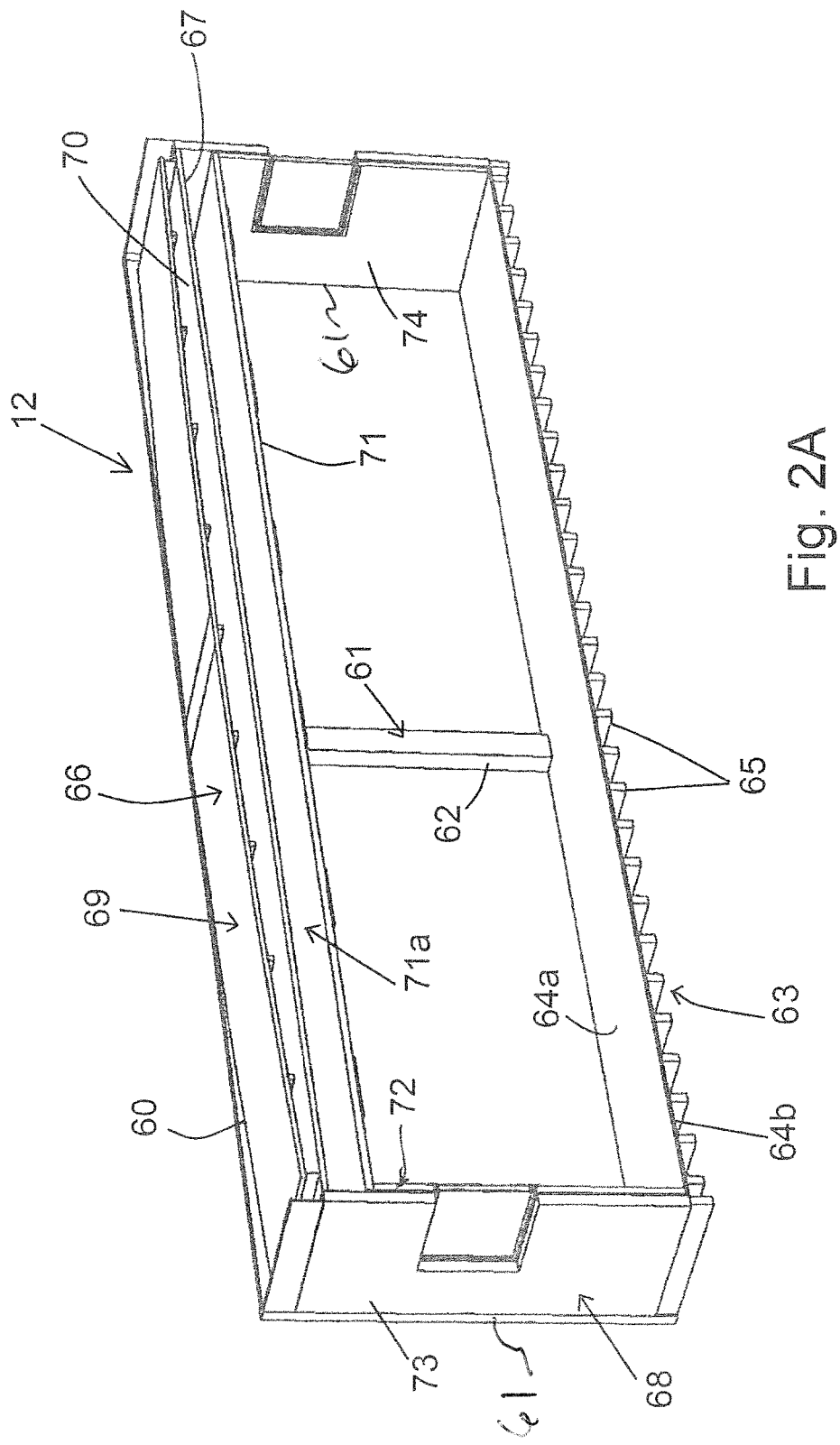
FIGS. 2A and 2B represent partial cross-sectional views of an elementary module illustrating the design of the rigid frame and of the walls making up the external walls of this module.
Figure 2B:
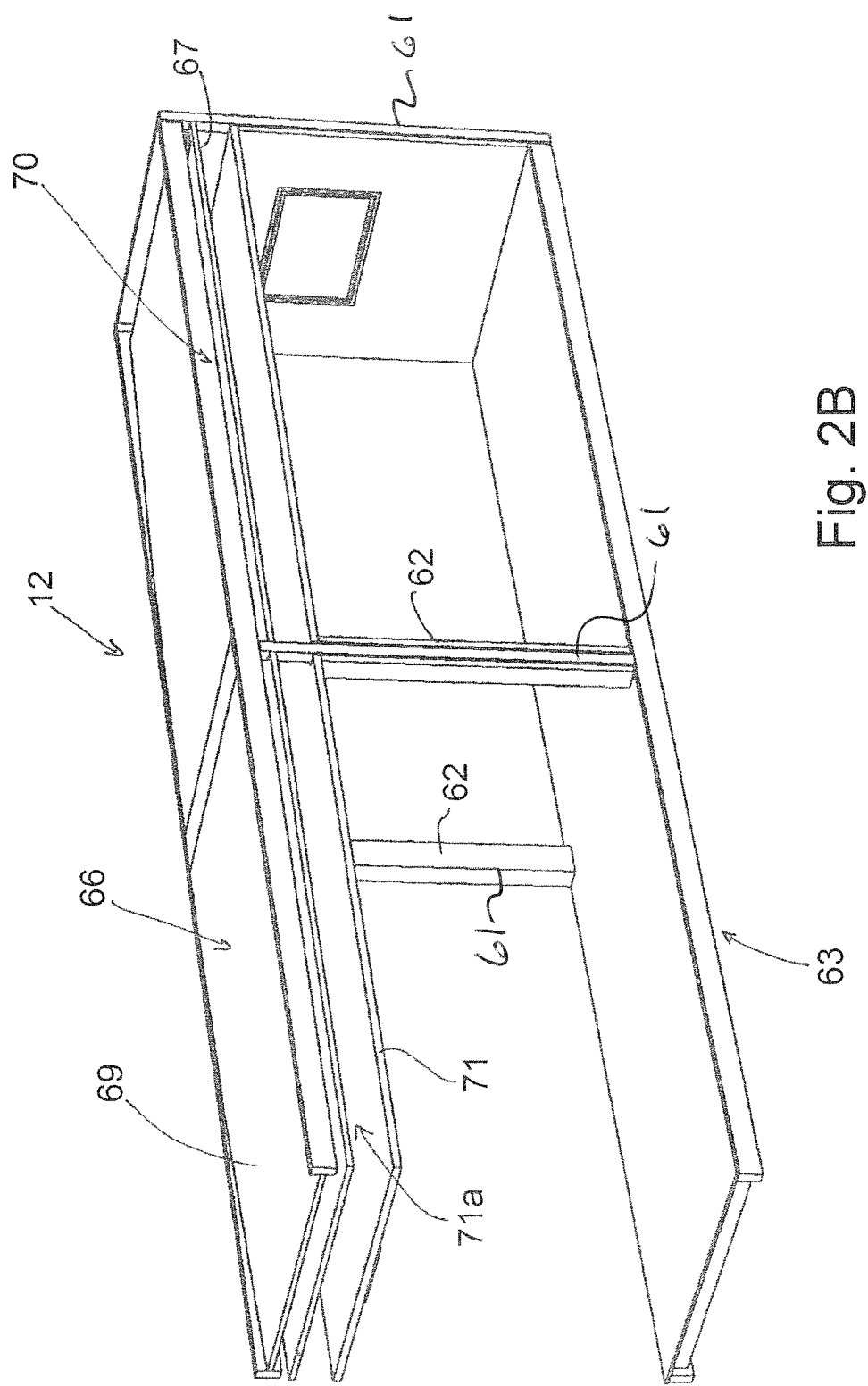
Figure 3:
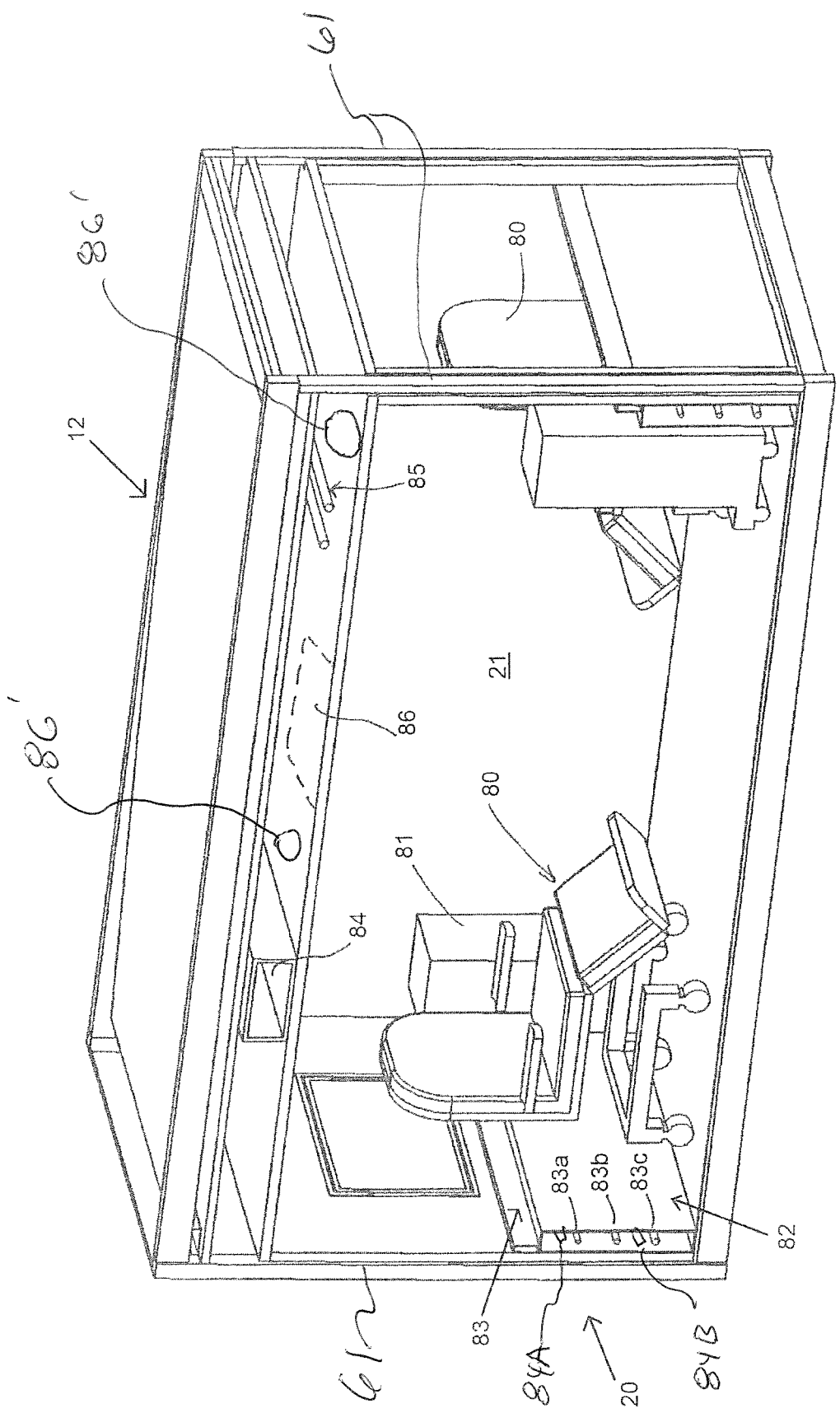
FIG. 3 is a perspective view of a preferred embodiment of a basic care room for a care unit according to the invention.

Referring to FIGS. 1 to 3, in particular to FIG. 1, center 10 for hemodialysis patients treatment describes below is built in a housing structure 11 that groups a plurality of elementary modules 12 built substantially the same way. Elementary modules 12 are represented more in detail in FIGS. 2A and 2B. They are juxtaposed in their width or in their length and they can be arranged inside, individually or in combination, to form, on the one hand, one or several care rooms for a hemodialysis treatment of patients, and, on the other hand, dedicated rooms arranged respectively to ensure the reception of the patients, the administrative follow-up of the patients, the medical follow-up of the patients, the storage of the raw materials, the individual preparation of the treatment solutions adapted to the patients, the preparation and control of the fluids used in said care room and/or the reprocessing and/or disposal of the residual waste and effluents generated in particular by said treatment of the patients.

Care room 20 is advantageously made of individual or double cells, which are arranged in one or several elementary modules 12. These elementary modules 12 can be adapted to the needs according to the location of the treatment centers, to the geography of the installation sites and/or to the data relating to the local population and conditions.

FIG. 1 represents a hemodialysis patients treatment center 10 comprising a building with a substantially rectangular shape, called housing structure 11, and which is preferably mounted on a flat plate that serves as a support for a plurality of elementary modules 12. Elementary modules 12 are advantageously boxes or containers (see FIGS. 2A and 2B) or the like, with a parallelepipedic shape, whose dimensions are adapted to allow a simple transport and a cost-effective layout, while still remaining efficient, and to allow the installation in an individual or grouped form of all the required equipment. This equipment is on the one hand intended and designed to make up at least one care room 20 intended for treating the patients or at least one dedicated room 30 intended for grouping the components suitable for one or several ancillary functions indispensable before, during of after the treatment of the patients.

Treatment unit 10 as a whole is arranged around a central section made of care room 20 formed by one or several basic care cells 21. A basic care cell 21 is illustrated and will be described in detail referring to FIG. 3. In the represented example, care room 20 comprises at least one subdivision 40 assigned to patients requiring specific precautions, in particular patients contaminated by dangerous viruses, which are at risk of propagating and contaminating the caregivers and/or other patients.

The access to the care room is reserved for the patients who have previously been received in a reception zone 13 by a reception staff. The reception zone is organized to take in charge the administrative management of the patients, that is to say the registration, the appointments and to direct them to a waiting room 14. The patients are then taken over by a medical division 15 that is arranged to make the required medical analyses and ensure the medical follow-up, to make sure that all possibly required preparatory medical steps are carried out before the beginning of a treatment sequence in the care room.

Various zones for the caregivers, such as for example a change room and a preparation room 16, a canteen or company restaurant 17 and ancillary rooms 18 to allow the patients to change and put on the patient coats or the like, a sanitary facilities room 19 and an indispensable rest room 40, where the patients stay for a given period after their treatment, are also installed close to reception zone 13, before care room 12.

The patients are treated in one of basic care cells 21 or in one of special subdivisions 40 of care room 20 according to the decisions made by the medical division. The preparation of the treatment solutions, the fluids and temperature control, the electrical energy supply, the supply and treatment of the dialysis water, the management of the fluids and pharmaceutical products stocks are organized in another section of center 10, preferably in dedicated rooms 30, which are installed in elementary modules 12, coupled and combined with each other, installed in rooms specifically dedicated to the various functions defined above. The coupling and the combination of elementary modules 12 occur by putting in place separating walls that allow separating the necessary spaces so they can fulfill their functions. The whole of said dedicated rooms that could also be qualified as service rooms is advantageously arranged on the other side of care room 20 with respect to the reception service and the medical patients preparation service.

Among the rooms grouped under the general name of dedicated rooms 30, one can mention:
- a room 31a comprising water treatment means;
- a room 31b for storing treated water to ensure sufficient autonomy of care unit 10;
- a room 32 that groups the concentrate stocks intended to be diluted by hemodialysis generators, and used as the base for all hemodialysis treatments;
- a room 33 for storing pharmaceutical products that are likely to be used by a patient before, during or after a treatment;
- a room 34 for the management and, in case of a failure of an electrical power supply network, for the production of electrical energy;
- a room 35 for storing chemicals, in particular for the cleaning and disinfection of the installations and equipments;
- a room 36 for treating and/or inerting and/or eliminating the waste produced by the treatment; and
- a room for storing technical parts to ensure equipment maintenance.

An electrical energy production unit could be mounted for safety purposes in an additional dedicated room 30, which would have the particularity of being located outside. The same applies to a purified air production unit, a heat exchange device for generating, according to the needs, heated fluids or refrigerated fluids, in particular for heating and/or air conditioning. This equipment could, according to the case, be mounted in additional elementary modules separated from housing structure 11 of treatment center 10.

FIGS. 2A and 2B represent an elementary module 12 in a longitudinal cross-sectional perspective view for FIG. 2A and open at one end for 2B. An elementary module 12 is substantially designed as a container 60 with a parallelepipedic shape comprising a rigid frame 61 made, for example, with at least four metal beams 62 manufactured in the form of profiles out of galvanized steel or the like, on which is mounted, on the one hand, a bottom 63 in the form of a wooden floor or a plate out of vibrated concrete or the like 64a associated with a rodent protection steel sheet 64b located towards the outside, carried by strengtheners in the form of metal beams 65 and, on the other hand, a ceiling 66, preferably made of a flat galvanized steel sheet 67. Then, according to the needs of unit 10, an elementary module can be used independently or in combination with other identical elementary modules and closing walls or separating walls 68, on one, two or three sides, which can be put in place according to the needs imposed by the planned layout. The roof of elementary module 12 is covered with a galvanized steel sheet 69, which is curved to ensure the runoff of rainwater and arranged to leave a space 70 with respect to galvanized steel sheet 67 of ceiling 66 and the roof 69. This space 70 is filled with an insulating material, for example glass wool of a thickness of the order of 200 mm, or any other suitable insulating material.

It must be noted that elementary module 12 is equipped with a false ceiling 71, located vertically below the ceiling 66, in the form of a parallel panel that defines, with the galvanized steel sheet 67 of ceiling 66, a technical plenum 71a that can be used for various equipments such as the forced air circulation network, the electrical wiring circuits, the air conditioning, conduit, etc. The side walls are advantageously made of multilayer panels 72 with a weatherproof protective external layer 73, one or several intermediate layers out of insulating materials such as for example polyurethane foam and an internal coating approved for clean rooms. In a general way, all internal coatings, and more specifically all internal coatings 74 that correspond to the care room or to sensitive rooms are made out of materials approved for the coating of clean rooms.

FIG. 3 illustrates an embodiment of a care room 20 made of at least one basic care cell 21 arranged in an elementary module 12. This is, in fact, a double care room, i.e., arranged to receive and treat simultaneously two patients. For this purpose, the basic care cell 21 comprises two treatment seats 80, which could be beds or armchairs, arranged at the two longitudinal ends of module 12, facing each other. They can be separated by a removable curtain or by a screen (not represented) in order to respect the privacy of each of the patients. A hemodialysis generator 81 is associated to each of said seats 80. A technical fluid distribution through 82 and a cable trough 83 are mounted behind each seat, to allow supplying the energy, the communication data and the liquids used during the treatment, on the one hand, to the dialysis generator and, on the other hand, to all appliances and/or equipment required during this treatment. Trough 82 advantageously contains, on the one hand, a conditioned air blowing circuit 84a and a return circuit for this conditioned air 84b. Trough 82, moreover, contains a hemodialysis water supply 83a, a dialysis concentrates supply 83b, and a hemodialysis liquid outlet pipe 83c for its discharge. Wiring trough 83 contains electrical supply cables for the dialysis generator 81 and for the electrical equipment of seat 80. Communication cables to connect the seat 80 and the hemodialysis generator to a computerized data management center are also housed in said wiring trough 83. The hemodialysis generator is designed to be supplied with hemodialysis water at supply port 83a, with concentrate at supply port 83b or by means 5 or 10 liter canisters, so that the concentrate can for example be different from that of the network, to be adapted to the patient. Trough 82, moreover, has the possibility to communicate by means of suitable ducts (not represented) with an air blowing duct 84 and an air return grille 86 arranged in the false ceiling. For this purpose, trough 82 contains an air supply duct 84a and a return duct 84b for air regeneration. Refrigerated or heated water circuits 85 are arranged in the false ceiling, to allow cooling or heating of the air according to accommodate the needs and evacuating the air through air return grille 86 arranged in the false ceiling Furthermore, one will note that false ceiling 71 allows creating said empty space 70 that contains an air supply duct 84 and a return duct 86 in care room 20. A refrigerated or heated water circulation circuit 85 allows cooling or heating the ambient atmosphere in care room 20. A conditioned air outlet grille 86 is arranged in the closing plate of false ceiling 71. Conventional lighting 86' is arranged in the closing plate of the false ceiling 71.

Figure 4:
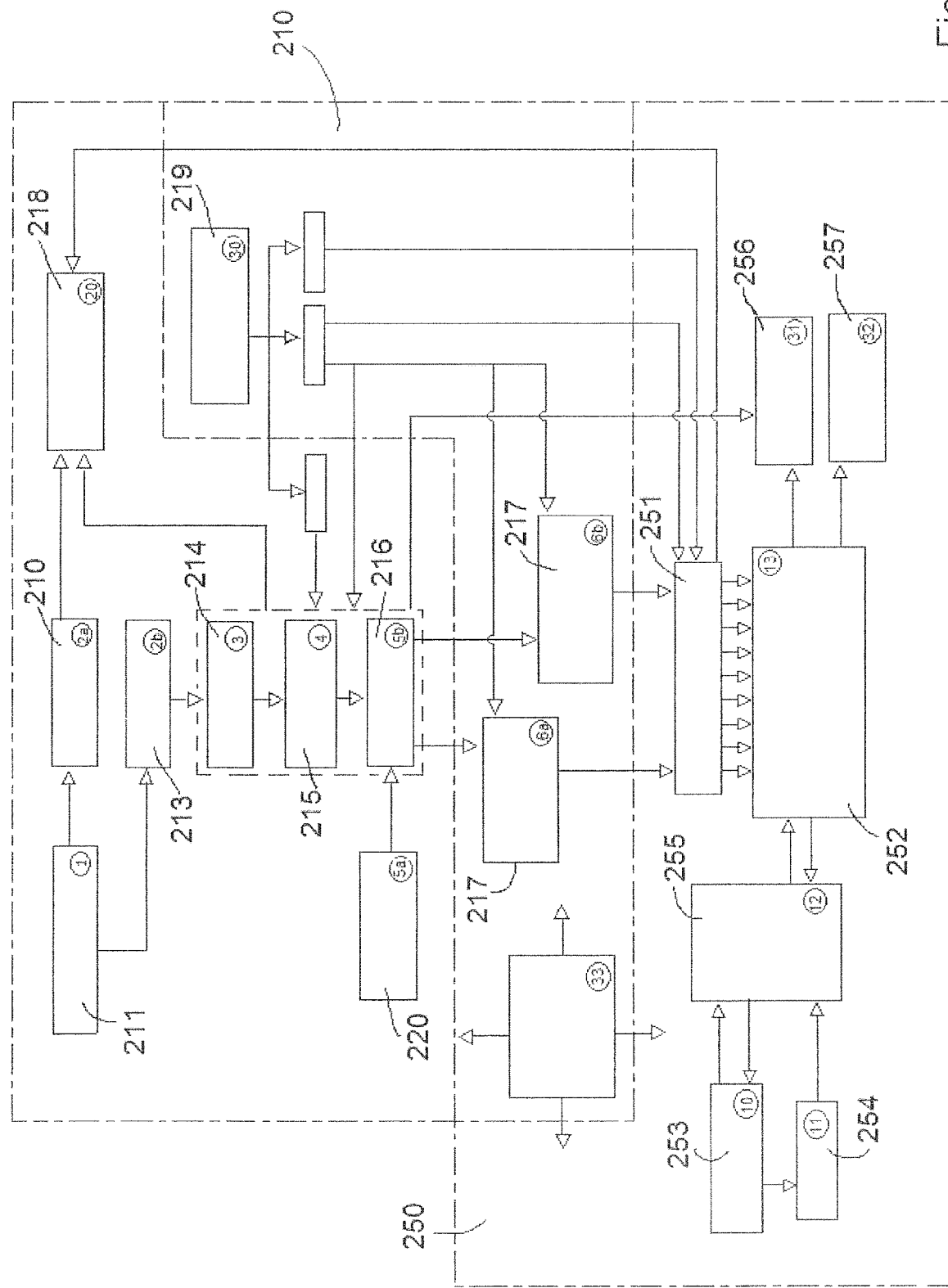
FIG. 4 is an operating diagram of a hemodialysis care unit combined with a dedicated treatment products production service.

FIG. 4 illustrates an evolution of the concept for an adaptation to smaller or remote hemodialysis patients treatment units, which include both the structures allowing the preparation of the treatment products and the structures adapted for the treatment and follow-up of the patients. For this purpose, the schematically illustrated device 200 is made of two units 210 and 250, which are respectively assigned to products preparation and to patients care. Products preparation unit 210 comprises means 211 for receiving and storing the raw materials, a removal unit 212, a weighing 213, a preparation equipment 214, a filtration unit 215 and a filling unit 216 for the containers intended for concentrates storage. The concentrates can be stored in canisters with for example a capacity of 5 and 10 liters, or in 800 or 1000 liter tanks.

Together with these services, storing means 217 may be provided for the conditioning items in view of their reutilization after use. An analysis laboratory 218 completes this equipment to ensure the quality of the prepared substances. A purified water preparation unit 219 is integrated in unit 210. Air treatment means 220 can also be provided. They can be assigned as well to products preparation unit 210 as to care unit 250.

Care unit 250 mainly comprises a dialysis generator 251 that is directly coupled to a care room 252, which is for example a common room equipped with screens or internal room dividers. Care room 252 is provided with individual treatment armchairs separated by curtains or screens. Some individual beds may be provided for special or severe cases. A reception structure 253 is located at the entrance of care room 252 to receive the patients and direct them in the center. A consultation room 254 for doctors is attached to reception 253. A changing room 255 for the patients is attached to reception 253. Technical rooms for effluents neutralization 256 and waste incineration 257 are located at the exit of care room 252. Dialysis generator 251 is directly connected to dialysis concentrates storage means 217 and to purified water preparation unit 219 in order to adapt the treatment products according to the patients, taking the results of the analyses into consideration.

The invention is not restricted to the examples of embodiment described and can present different aspects according to certain foreseeable evolutions or according to specific needs. The dimensions of the care room, its layout, in particular the arrangement of the treatment armchairs or the arrangement of the dedicated rooms assigned to the various ancillary services may be modified according to the local needs or availabilities. However, the scope of these modifications is restricted to transformations which are obvious to a person skilled in the art. In particular technical trough 82 can be made either in partial sections having the dimension of each module or have the dimension of several modules with pluggable connections between modules, to receive the various wired electrical circuits for the high-voltage and low-voltage currents, the fluids networks and the ducts for the conditioned aeraulic circuits.

The invention claimed is:

1. An autonomous treatment unit (10, 200) for treating at least a plurality of patients by hemodialysis, the unit (10, 200) being an individual construction comprising:
    at least one care room equipped with a dialysis generator, and the dialysis generator being arranged to prepare treatment solutions adapted to treat each individual patient of the plurality of patients, and
    at least one care room containing the treatment solutions which are prepared by dilution of at least one concentrate, made of at least one solid water-soluble compound, with hemodialysis water, and the solid water-soluble compound comprising at least one of sodium chloride (NaCl), potassium chloride (KCl), calcium chloride ($CaCl_2$), and magnesium chloride, ($MgCl_2$),
    wherein treatment unit (10, 200) is built into a housing structure grouping a plurality of elementary modules built substantially in a same way, arranged juxtaposed and in a combination, to form a first group of service rooms (210) assigned to provide for a hemodialysis treatment of each one of the plurality of patients, with the first group of service rooms having dedicated rooms arranged for reception of the plurality of patients, administrative follow-up of the plurality of patients and medical follow-up of the plurality of patients,
    a second group of technical rooms (250) for preparation and storage of the concentrates, for preparation and control of the fluids used in the at least one care room and/or the reprocessing and/or disposal of residual and effluents generated during treatments of the plurality of patients, and
    each of the elementary modules forming the housing structure comprises a parallelepipedic shape container which comprises a rigid frame, the rigid frame supports at least one side wall, a bottom floor and a roof with a ceiling located adjacent but spaced from the roof, an insulating material is accommodated within the space located between the roof and the ceiling, and a false ceiling is located vertically below the ceiling for accommodating at least one of a forced air circulation network, electrical wiring, air conditioning and conduit, and a trough which contains at least a hemodialysis water supply, a dialysis concentrates supply, and a hemodialysis liquid outlet pipe for discharging fluid.

2. The autonomous treatment unit (200) according to claim 1, wherein each elementary module has a rigid support located in each corner thereof which is connected with the bottom floor, the roof, the ceiling and the false ceiling.

3. The autonomous treatment unit (200) according to claim 1, wherein the rigid frame has a metal beam in each corner and at least one metal beam located between a pair of metal beam located in opposite corners of the container.

4. The autonomous treatment unit (200) according to claim 1, wherein the technical room (210) comprises a removal unit (212), weighing means (213), a preparation unit for the patient's treatment solutions (214), a filtration unit (215) and a unit (216) for filling the containers intended for concentrates storage.

* * * * *